(12) United States Patent
Ilan et al.

(10) Patent No.: US 11,020,101 B2
(45) Date of Patent: *Jun. 1, 2021

(54) DEVICE AND METHOD FOR THE APPLICATION OF A CURABLE FLUID COMPOSITION TO A BODILY ORGAN

(71) Applicant: Omrix Biopharmaceuticals Ltd., Rehovot (IL)

(72) Inventors: Erez Ilan, Kibbutz Netzer Sereni (IL); Yotam Gurman, Kibbutz or Haner (IL); Moti Meron, Herzliah (IL)

(73) Assignee: Omrix Biopharmaceuticals Ltd., Rehovot (IL)

( * ) Notice: Subject to any disclaimer, the term of this patent is extended or adjusted under 35 U.S.C. 154(b) by 68 days.

This patent is subject to a terminal disclaimer.

(21) Appl. No.: 16/170,205

(22) Filed: Oct. 25, 2018

(65) Prior Publication Data

US 2019/0076137 A1 Mar. 14, 2019

Related U.S. Application Data

(62) Division of application No. 13/780,316, filed on Feb. 28, 2013, now Pat. No. 10,130,346.

(30) Foreign Application Priority Data

Jul. 24, 2012 (IL) .......................................... 221079

(51) Int. Cl.
*A61B 17/00* (2006.01)
*A61B 17/11* (2006.01)

(52) U.S. Cl.
CPC .... *A61B 17/0057* (2013.01); *A61B 17/00491* (2013.01); *A61B 2017/005* (2013.01); *A61B 2017/1107* (2013.01)

(58) Field of Classification Search
CPC .......... A61B 17/0057; A61B 17/00491; A61B 2017/005; A61B 2017/1107

(Continued)

(56) References Cited

U.S. PATENT DOCUMENTS 4,401,492 A * 8/1983 Pfrommer ................. A61F 2/52
156/145
5,254,113 A * 10/1993 Wilk .................... A61B 17/1114
128/898

(Continued)

*Primary Examiner* — Amy R Weisberg
(74) *Attorney, Agent, or Firm* — David R. Crichton

(57) ABSTRACT

The invention relates to a device suitable for application of a curable fluid composition to encircle a bodily organ. The device comprises a monolithic piece of a flexible material having a length dimension with an inner surface and an outer surface, a first end and a second end, a width dimension, and two spaced-apart sides, wherein a portion of the length dimension proximal to the first end is configured to contact a portion of the length dimension proximal to the second end, the inner surface defining a hollow area between the two spaced-apart sides; and at least one inlet providing fluid communication between the outer surface and the inner surface, for introduction of the fluid into the hollow area. The device deployable around the bodily organ such that when the portion of the length dimension proximal to the first end contacts the portion of the length dimension proximal to the second end, an outer surface of the bodily organ and the hollowed area define an enclosed volume encircling the bodily organ, the enclosed volume suitable for containing the fluid therein.

16 Claims, 4 Drawing Sheets

(58) Field of Classification Search
USPC .................. 606/214, 74, 151, 201; 600/37
See application file for complete search history.

(56) References Cited

U.S. PATENT DOCUMENTS

| | | | | |
|---|---|---|---|---|
| 5,749,895 A * | 5/1998 | Sawyer | ............ | A61B 17/00491 606/214 |
| 5,895,412 A * | 4/1999 | Tucker | ............ | A61B 17/00491 606/215 |
| 6,652,559 B1 * | 11/2003 | Tetreault | .............. | A61B 17/085 606/213 |
| 7,066,960 B1 * | 6/2006 | Dickman | ................ | A61F 2/441 623/13.11 |
| 8,535,349 B2 * | 9/2013 | Chen | .................. | A61B 17/0057 606/213 |
| 9,119,606 B2 * | 9/2015 | Weadock | ............ | A61B 17/1155 |
| 2002/0193659 A1 * | 12/2002 | Yachia | ...................... | A61F 2/26 600/39 |
| 2003/0013989 A1 * | 1/2003 | Obermiller | ........ | A61B 17/0057 600/567 |
| 2004/0215231 A1 * | 10/2004 | Fortune | .................. | A61B 17/11 606/213 |
| 2005/0004158 A1 * | 1/2005 | Iyer | .................... | A61B 17/0057 514/291 |
| 2005/0118156 A1 * | 6/2005 | Woolverton | ......... | A61K 38/363 424/94.6 |
| 2006/0085031 A1 * | 4/2006 | Bettuchi | ................ | A61B 17/11 606/215 |
| 2006/0241763 A1 * | 10/2006 | Paul | .......................... | A61F 2/28 623/17.11 |
| 2007/0088445 A1 * | 4/2007 | Patel | .................. | A61B 17/0057 623/23.64 |
| 2007/0112361 A1 * | 5/2007 | Schonholz | ......... | A61B 17/0057 606/151 |
| 2007/0112428 A1 * | 5/2007 | Lancial | ................. | A61F 2/4405 623/17.12 |
| 2008/0004657 A1 * | 1/2008 | Obermiller | ........ | A61B 17/0057 606/213 |
| 2008/0015481 A1 * | 1/2008 | Bergin | ................ | A61B 17/0057 602/46 |
| 2008/0027477 A1 * | 1/2008 | Obermiller | ........ | A61B 17/0057 606/191 |
| 2008/0071310 A1 * | 3/2008 | Hoffman | ............ | A61B 17/0057 606/215 |
| 2009/0149958 A1 * | 6/2009 | Prewett | .................... | A61F 2/442 623/17.16 |
| 2009/0326577 A1 * | 12/2009 | Johnson | ............. | A61B 17/0057 606/213 |
| 2010/0030246 A1 * | 2/2010 | Pavcnik | ............ | A61B 17/0057 606/157 |
| 2010/0137902 A1 * | 6/2010 | Lee | ....................... | A61L 24/001 606/213 |
| 2010/0256671 A1 * | 10/2010 | Falus | .................. | A61L 24/0031 606/214 |
| 2010/0256765 A1 * | 10/2010 | Butler | .................. | A61B 17/0642 623/17.16 |
| 2010/0284998 A1 * | 11/2010 | Smith | .................... | A61L 24/001 424/94.64 |
| 2010/0286716 A1 * | 11/2010 | Ford | .................. | A61B 17/0057 606/151 |
| 2011/0004306 A1 * | 1/2011 | Harper | ................. | A61B 17/0057 623/14.13 |
| 2011/0060277 A1 * | 3/2011 | Lilley | ............... | A61B 17/00491 604/104 |
| 2011/0087270 A1 * | 4/2011 | Penner | .................. | A61B 17/0057 606/213 |
| 2011/0087271 A1 * | 4/2011 | Sargeant | ............ | A61B 17/0057 606/213 |
| 2011/0087272 A1 * | 4/2011 | Sargeant | ............ | A61B 17/0057 606/213 |
| 2011/0125187 A1 * | 5/2011 | Soltz | ................ | A61B 17/00491 606/214 |
| 2011/0172760 A1 * | 7/2011 | Anderson | .......... | A61B 17/0057 623/1.15 |
| 2011/0196420 A1 * | 8/2011 | Ebner | .................. | A61M 1/0088 606/213 |
| 2011/0238097 A1 | 9/2011 | Bettuchi | | |
| 2011/0270284 A1 * | 11/2011 | Beauchamp | .......... | A61F 2/0063 606/151 |
| 2011/0282448 A1 * | 11/2011 | Paulos | .................. | A61L 15/325 623/13.11 |
| 2011/0313406 A1 * | 12/2011 | Fortier | .................... | A61B 17/11 606/1 |
| 2011/0319915 A1 * | 12/2011 | Viola | ................ | A61B 17/00234 606/151 |
| 2012/0010653 A1 * | 1/2012 | Seifert | ............... | A61B 17/0057 606/213 |
| 2012/0035610 A1 * | 2/2012 | Deslauriers | ...... | A61B 17/00491 606/93 |
| 2012/0059411 A1 * | 3/2012 | Sun | ..................... | A61B 17/0057 606/213 |
| 2012/0065650 A1 * | 3/2012 | Amato | ............... | A61B 17/0057 606/151 |
| 2012/0116300 A1 | 5/2012 | Banks, Jr. | | |
| 2012/0165957 A1 * | 6/2012 | Everland | ............... | A61F 2/0045 623/23.72 |
| 2012/0316583 A1 * | 12/2012 | Christoudias | .... | A61B 17/00234 606/151 |
| 2013/0006301 A1 * | 1/2013 | Sargeant | .......... | A61B 17/00491 606/214 |
| 2013/0144249 A1 * | 6/2013 | Fenton | ............. | A61B 17/00491 604/500 |
| 2013/0204277 A1 * | 8/2013 | Fabry | .................. | A61B 17/0057 606/151 |
| 2013/0310779 A1 * | 11/2013 | Wnek | ................ | A61B 17/0057 604/319 |
| 2013/0317527 A1 * | 11/2013 | Jacinto | ............... | A61B 17/0057 606/151 |
| 2014/0066979 A1 * | 3/2014 | Jonsson | ............. | A61B 17/0057 606/213 |
| 2014/0081415 A1 * | 3/2014 | Ruberti | ................... | A61B 17/11 623/23.7 |
| 2014/0088642 A1 * | 3/2014 | Ilan | .................. | A61B 17/00491 606/214 |
| 2014/0148827 A1 * | 5/2014 | Odermatt | ............... | A61F 2/0063 606/151 |
| 2014/0163606 A1 * | 6/2014 | Ragg | .................. | A61B 17/0057 606/201 |
| 2014/0188141 A1 * | 7/2014 | Ilan | .................. | A61B 17/00491 606/153 |
| 2014/0236274 A1 * | 8/2014 | Dickinson | .......... | A61B 17/3478 623/1.11 |
| 2014/0263563 A1 * | 9/2014 | Stokes | ................ | A61B 17/1155 227/179.1 |
| 2014/0350580 A1 * | 11/2014 | Bell | .................... | A61B 17/0057 606/151 |
| 2014/0379005 A1 * | 12/2014 | Trabucco | ................ | A61F 2/0063 606/151 |
| 2015/0051532 A1 * | 2/2015 | Tomko | ................ | A61M 1/3661 604/8 |
| 2015/0157436 A1 * | 6/2015 | Bailly | ................... | A61F 2/0063 606/151 |
| 2015/0299359 A1 * | 10/2015 | Shandas | ................ | A61F 2/0063 606/151 |
| 2015/0351730 A1 * | 12/2015 | Stokes | ............. | A61B 17/12136 606/213 |

* cited by examiner

DEVICE AND METHOD FOR THE APPLICATION OF A CURABLE FLUID COMPOSITION TO A BODILY ORGAN

This application is a divisional application of co-pending U.S. patent application Ser. No. 13/780,316 filed on Feb. 28, 2013 which claims priority to U.S. Provisional Patent Application No. 61/675,206 filed on Jul. 24, 2012 and claims benefit of Israel Patent Application 221079 filed Jul. 24, 2012. The complete disclosures of the aforementioned related U.S. patent applications are hereby incorporated herein by reference for all purposes.

FIELD OF THE INVENTION

The invention relates to the field of devices for application of a curable fluid composition to a bodily organ, and more particularly, to a device for applying a curable fluid composition to encircle a bodily organ, and methods of use thereof.

BACKGROUND OF THE INVENTION

Application of sealant, such as fibrin sealant, is useful for preventing leakage of fluids, such as air and/or liquid from tissues. In surgical procedures, fibrin sealant may be applied to wounds, including bleeding or non-bleeding wounds in a bodily organ e.g. by dripping or spraying the sealant onto the wound. For example, fibrin sealant can be used during an anastomosis procedure, wherein the organ is sutured or stapled around the entire incision line and fibrin sealant is applied along the staple or suture line for reinforcement and to prevent leakage.

Fibrin sealant is typically a plasma derived product obtained from either commercial sources or some regional blood transfusion centers. Components that are commonly used in preparations of fibrin sealants are predominantly a fibrinogen component [supplemented with various quantities of Factor VIII, Factor XIII, fibronectin, vitronectin and von Willebrand factor (vWF)] and a thrombin component. The fibrinogen component is typically activated by the thrombin component which is the last protease of the coagulation cascade.

Fibrin sealant is formed by an enzymatic reaction involving inter alia, fibrinogen, thrombin and Factor XIII. The thrombin converts the fibrinogen to fibrin by enzymatic action at a rate determined by the concentration of thrombin. Factor XIII, is typically present in the fibrinogen component of the sealant and is an enzyme of the blood coagulation system that cross-links and stabilizes the fibrin clot. This process bypasses most of the steps of normal coagulation and mimics its last phase. Some manufacturers add antiproteolytic agents to the fibrin sealant formulation (as described in WO 93/05822) or specifically remove the plasminogen in order to stop or delay the fibrinolysis (as described in U.S. Pat. Nos. 5,792,835 and 7,125,569).

Fibrin sealant is commonly applied by spraying the fibrinogen component and the thrombin component by air assisted spraying, airless spray, or by dripping application.

Air assisted spraying from a close proximity is challenging due to effect of air on pre-cured fibrin which yields a variable fibrin layer with irregularities (i.e. thick and thin areas) and uncovered regions at the application site.

In situations when the space around the organ is limited and an angular and long tip is required to reach the target area, the edge of the tip may be positioned too close to the tissue surface such that adequate spraying is not attainable. Furthermore, airless spray applicators and air assisted spray applicators may clog.

In dripping application of fibrin sealant, difficulties are encountered due to dripping against gravity when applying the substance to the lower part of the organ.

Application of fibrin around an entire circumference of a bodily organ by spraying or dripping is problematic since complete coverage around the organ is very difficult to achieve due to inaccessibility of at least a part of the organ within the body e.g. the lower part of the organ.

In addition, the layer formed around the organ has uneven thickness, resulting in stronger and weaker areas of seal. Thus, application of a uniform layer is very difficult to achieve.

US 2011/0238097 discloses an apparatus for applying sealant to a target tissue of a luminal tissue at a surgical site. The apparatus includes a handle, conduit and an end effector e.g. a clamp, which may comprise two jaw members. The handle has means configured and adapted for operating the end effector and dispensing biological sealant to the surgical site via the end effector. A mechanism to open and close the device is typically located in a handle to cause approximating the ends of the jaws one to the other to wrap around the tissue. The conduit stores and/or carries sealant towards the end effector.

SUMMARY OF THE INVENTION

The invention, in some embodiments thereof, relates to a device for applying a curable fluid composition to encircle a bodily organ, and methods of use thereof.

Aspects and embodiments of the invention are described in the specification hereinbelow and in the appended claims.

According to an aspect of some embodiments of the invention, there is provided a device [10, 40] suitable for application of a curable fluid composition to encircle a bodily organ, the device comprising a monolithic piece of a flexible material [12] having a length dimension [14] with a first end [22] and a second end [24], an inner surface [18] and an outer surface [20], a width dimension [16], and two spaced-apart sides [26a, 26b], wherein a portion of the length dimension [14] proximal to the first end [22] is configured to contact a portion of the length dimension [14] proximal to the second end [24]. The inner surface [18] defines a hollow area [31] between the two spaced-apart sides [26a, 26b]. The device further comprises at least one inlet [28] providing fluid communication between the outer surface [20] and the inner surface [18], for introduction of fluid into the hollow area [31]. The device [10, 40] is deployable around the bodily organ [30] such that when the portion of the length dimension proximal to the first end [22] contacts the portion of the length dimension proximal to the second end [24], an outer surface [33] of the bodily organ [30] and the hollowed area [31] define an enclosed volume [32] encircling the bodily organ [30], the enclosed volume [32] being suitable for containing the fluid therein.

In some embodiments, the piece of flexible material is biased to curl to form a planar spiral, such that a portion of the length dimension proximal to the first end overlaps a portion of the length dimension proximal to the second end when unconstrained.

In some embodiments, the device is configured so that when deployed around the bodily organ, a portion of the length dimension between the first end and the second end encircles the bodily organ, and an inner surface of the piece of flexible material proximal to the first end intimately contacts an inner surface of the piece of flexible material proximal to the second end, thereby defining the enclosed volume.

In some embodiments, the piece of flexible material is straight when unconstrained.

In some embodiments, the device further comprises a plurality of raised, parallel, spaced-apart bands [42] along at least a portion of the outer surface, arranged substantially perpendicular to the length dimension, for providing mechanical strength. In some such embodiments, each band has a height in the range of from 1 to 7 mm, a width in the range of from 1 to 10 mm, and a length in the range of from 28 to 34 mm (or to fit the entire width of the device).

In some embodiments, the device further comprises at least one plastically deformable strip [44] attached to the inner surface. In some embodiments, the device further comprises two plastically deformable strips, each attached to one of the two spaced-apart sides. In some embodiments, the plastically deformable strips comprise a metal.

In some embodiments, the width of the piece of flexible material is substantially constant along the length dimension. In some embodiments, the width of the piece of flexible material proximal to the second end is less than the width proximal to the first end.

In some embodiments, the device comprises at least two inlets.

In some embodiments, the curable fluid composition comprises at least two components. In some embodiments, a first of at least two components is activated by a second of at least two components. In some such embodiments, the first component comprises fibrinogen. In some such embodiments comprising fibrinogen, the second component, for activation of fibrinogen, comprises thrombin. In some such embodiments, a concentration of fibrinogen is 51.5 mg/ml and a concentration of thrombin is 180 IU/ml.

In some embodiments, the flexible material is selected from the group consisting of a non-biodegradable material (such as, for example, at least one of silicone rubber, fluoroelastomer, polychloroprene, and combinations thereof), a biodegradable material (such as, for example, at least one of collagen, fibrin, gelatin and combinations thereof).

In some embodiments, the piece of flexible material along at least a portion of the length is in the range of from 1 to 8 cm wide, such as in the range of from 4 to 6 cm wide.

In some embodiments, the piece of flexible material is in the range of from 4 to 100 cm long, such as in the range of from 7 to 20 cm long.

In some embodiments, the bodily organ is a hollow organ. In some embodiments, the bodily organ is selected from the group consisting of a blood vessel, an organ of the digestive system, an organ of the urinary system, and a dura. In some embodiments, an organ of the digestive system is selected from the group consisting of an esophagus, a stomach, a small intestine (such as, for example, a duodenum, a jejunum, or an ileum), a large intestine (such as, for example, a colon, a cecum, a rectum, or an anus), a bowel, and a pancreas.

In some embodiments, wherein the organ of the digestive system is selected from the group consisting of an esophagus and a pylorus of the stomach of a human adult, the piece of flexible material is about 7 cm long.

In some embodiments, wherein the organ of the digestive system is the small intestine of a human adult, the piece of flexible material is about 13 cm long.

In some embodiments, wherein the organ of the digestive system is the large intestine of a human adult, the piece of flexible material is about 20 cm long.

According to some embodiments, the device of any of the embodiments described herein is provided for use in applying a curable fluid composition to encircle a bodily organ and/or for defining a chamber comprising an enclosed volume around an exposed bodily organ.

According to some embodiments, there is provided a method for applying a curable fluid composition to encircle a bodily organ [30], the method comprising providing a device according to any of the embodiments described herein, deploying the device around the bodily organ so that a portion of the length dimension proximal to the first end contacts a portion of the length dimension proximal to the second end, thereby defining, between an outer surface [33] of the bodily organ and the hollowed area, an enclosed volume encircling the bodily organ; and introducing the curable fluid composition into the enclosed volume through at least one inlet.

In some such embodiments, the curable fluid composition comprises at least two components, wherein the two components are introduced through the same of at least one inlet. In some such embodiments, the at least two components are introduced substantially simultaneously through at least one inlet. In some embodiments, the at least two components are introduced sequentially through at least one inlet.

In some embodiments, introducing the curable fluid composition comprises injecting the curable fluid composition through at least one inlet.

In some embodiments, the method further comprises allowing the curable fluid composition to cure. In some such embodiments, the method further comprises removing the device subsequent to curing of the curable fluid composition.

In some embodiments, the bodily organ is a hollow organ. In some such embodiments, the hollow organ is in a rigid state. In some such embodiments, the rigid state is achieved by inflation of the bodily organ with a fluid.

In some embodiments, the bodily organ is an anastomized bodily organ. In some such embodiments, the bodily organ is anastomized by a method selected from the group consisting stapling and suturing. In some embodiments, wherein the bodily organ is anastomized by stapling, the stapler is present in the organ during said applying of the curable fluid composition to provide a rigid state of the bodily organ.

According to some embodiments, there is provided a method for defining a chamber comprising an enclosed volume encircling an exposed bodily organ [30], the enclosed volume capable of retaining therein a curable fluid composition, the method comprising providing a device according to any of the embodiments described herein, deploying the device around the bodily organ so that a portion of the length dimension proximal to the first end contacts a portion of the length dimension proximal to the second end, thereby defining, between an outer surface [33] of the bodily organ and the hollowed area, an enclosed volume encircling the bodily organ.

The device according to the present invention has at least one of the following advantages: enables application of the curable fluid composition onto an entire outer cross-sectional dimension of a target organ e.g. a cylindrical organ; is sufficiently flexible to be easily conformed to the shape of the bodily organ; a single device may be self-adaptable for use with a range of bodily organs of different sizes and shapes, or at different locations on a non-uniform organ; enables uniform application of the curable fluid composition even on an area of a target organ which is difficult or impossible to access using other means; easy to use; cheap and simple to produce; enables application of a fluid to areas inaccessible to spray/drip and/or against gravity e.g. at the lower side of an organ; allows improved sealing strength relative to other application methods e.g. spray/drip; prevents leakage of the applied fluid (prior to curing) by providing a closed volume for containing the fluid; and has a short fluid path thereby eliminating and/or minimizing the risk of inlet blockage due to curing of the fluid. Furthermore, some embodiments of the device described herein can be used on a rigid and/or non-rigid organ.

The device and method described herein enable a user, such as a surgeon or other medical practitioner, to uniformly apply a curable fluid composition around a complete circumference of a bodily organ, without leakage of the substance out of the device prior to curing, and enable the user to easily apply the substance to sections of the organ which may be difficult or impossible to access using prior art methods, such as spray or drip application.

The device and method described herein are particularly useful for accurate application of a sealant, such as a fibrin sealant, to a bodily organ following anastomosis by suturing or stapling. The method described herein facilitates superior sealing and prevents leakage along the suture/staple line. The device and method described herein enable a desired volume of sealant to be applied, resulting in a seal of a desired height, width, and length.

In some embodiments, the sealant is formed in situ upon curing of a curable fluid composition. It was shown according to the present invention that optimal sealing strength is obtained with a fibrin sealant formed with a fibrinogen comprising component having 51.5 mg/ml fibrinogen and a thrombin comprising component having 180 IU/ml thrombin.

Unless otherwise defined, all technical and scientific terms used herein have the same meaning as commonly understood by one of ordinary skill in the art to which the invention pertains. In addition, the descriptions, materials, methods, and examples are illustrative only and not intended to be limiting. Methods and materials similar or equivalent to those described herein can be used in the practices of the present invention.

As used herein, the term "curable" in connection with a fluid composition, refers to a composition which can undergo an interaction between its components leading to an increase in viscosity of the composition. Such interactions include polymerization and/or cross-linking of components, achieved by means that include, but are not limited to, use of activating agents such as catalysts, or physical activators such as heat, radiation e.g. ultraviolet radiation, electron beams, or combinations thereof.

As used herein, the terms "comprising", "including", "having" and grammatical variants thereof are to be taken as specifying the stated features, integers, steps or components but do not preclude the addition of one or more additional features, integers, steps, components or groups thereof. These terms encompass the terms "consisting of" and "consisting essentially of".

As used herein, the indefinite articles "a" and "an" mean "at least one" or "one or more" unless the context clearly dictates otherwise.

BRIEF DESCRIPTION OF THE DRAWINGS

Some embodiments of the invention are described herein with reference to the accompanying figures. The description, together with the figures, makes apparent to a person having ordinary skill in the art how some embodiments of the invention may be practiced. The figures are for the purpose of illustrative discussion and no attempt is made to show structural details of an embodiment in more detail than is necessary for a fundamental understanding of the invention. For the sake of clarity, some objects depicted in the figures are not to scale.

In the Figures.

DESCRIPTION OF SOME EMBODIMENTS OF THE INVENTION

Figure 1A:
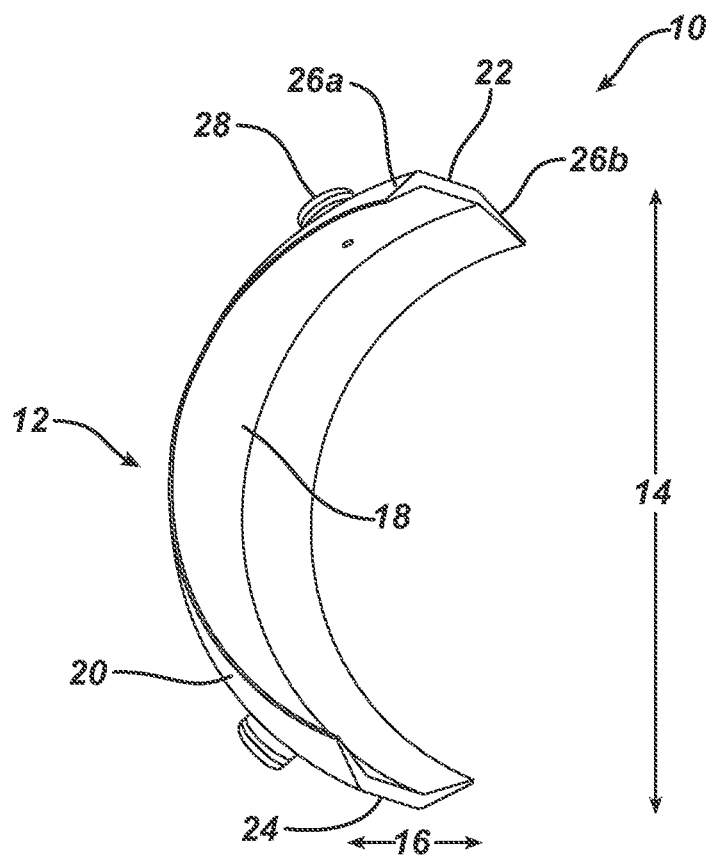
FIG. 1A is a perspective view of an embodiment of the device as described herein in an open, constrained configuration.

The invention, in some embodiments thereof, relates to a device for applying a curable fluid composition to encircle a bodily organ, and methods of use thereof.

The principles, uses and implementations of the teachings herein may be better understood with reference to the accompanying description and figures. Upon perusal of the description and figures present herein, one skilled in the art is able to implement the invention without undue effort or experimentation. In the figures, like reference numerals refer to like parts throughout.

Before explaining at least one embodiment in detail, it is to be understood that the invention is not necessarily limited in its application to the details of construction and the arrangement of the components and/or methods set forth in the following description and/or illustrated in the drawings. The invention is capable of other embodiments or of being practiced or carried out in various ways. The phraseology and terminology employed herein are for descriptive purpose and should not be regarded as limiting.

Referring now to FIGS. 1A-1D, there is shown an exemplary embodiment 10 of a device suitable for applying a curable fluid composition to encircle a bodily organ.

FIG. 1A is a perspective view of device 10, in an open, constrained configuration, prior to deployment on a bodily organ.

Device 10 comprises a monolithic piece of a flexible material 12, which can be unwound and constrained to provide a strip having a length dimension 14 and a width dimension 16, with an inner surface 18 and an outer surface 20, and two spaced-apart sides 26a, 26b, such that a hollow area 31 is defined between inner surface 18 and sides 26a and 26b. Length dimension 14 has a first end 22 and a second end 24.

Flexible material 12 is or may comprise any non-degradable or degradable material, optionally a synthetic or semi-synthetic material. The material is optionally any suitable biocompatible material. Examples of suitable materials include, but are not limited to, poly(ethylene); polyesters; poly(propylene), poly(propylene) polyesters such as poly (propylene) fumarate; polystyrene; polytetrafluoro ethylene (PTFE); nylon; polypropylene/cellulose; polypropylene/ PTFE; polypropylene/monochryal; polyester/collagen; poly (acrylate); poly(methyl methacrylate); poly(hydroxy ethyl methacrylate); poly(vinyl alcohol); poly(carbonate); poly (trimethylene carbonate); poly(ethyl ene-co-vinyl acetate); poly(ester urethane); poly(ether urethane); poly(arylate); poly(imide); poly(anhydride-co-imide); poly(amino acid); polydepsipeptide; poly(phosphazene); poly(glycolic acid); poly(lactide-co-glycolide); poly(lactic acid); poly(ε-capro lactone); poly(p-dioxanone); poly(lactide-co-glycolide); poly(ε-caprolactone-co-glycolide); poly(glycolide-co-trimethylene carbonate); lactide/tetramethylglycolide copolymer; lactide/trimethylene carbonate copolymer; lactide-δvalerolactone copolymer; poly(lactide)/polyethylene oxide copolymer; lactide (ε-captrolactone copolymer); unsymmetrically 3,6-substituted poly(1,4-dioxane-2,5-dione); poly (β-alkanoic acids) such as poly(β-hydroxybutyrate)/(β-hydroxyvalerate) copolymer, poly(β-hydroxybutyrate), poly (β-maleic acid) and poly β-hydroxypropionate), poly(δ-valerolatone); methylmethacrylate-N-vinyl pyrrolidone copolymer, polyesteramide; polyesters of oxalic acid; polydihydropyran; polyalkyl-2-cyanoacrylate; cellulosic materials; composites thereof; and combinations thereof.

In some embodiments, suitable biocompatible materials are optionally non-degradable materials selected from the group consisting of silicone rubber, fluoroelastomer, polychloroprene, and the like, or biodegradable materials selected from the group consisting of collagen, fibrin, gelatin and the like, or any combinations thereof.

Length dimension 14 of device 10 is optionally in the range of from about 4 to about 100 cm long, such as in the range of from about 7 to about 20 cm long. Width dimension 16 is optionally in the range of from about 1 to about 8 cm wide, or in the range of from about 4 to about 6 cm wide. Length dimension 14 is optionally from 0.5 to 100 times the width dimension 16.

Depending on the embodiment, width dimension 16 may be constant along the entire length dimension 14 of piece of material 12, or piece of material 12 may taper along length dimension 14 such that width dimension 16 is narrower at first end 22 than at second end 24. Piece of material 12 optionally has a thickness in the range of from about 0.3 to about 15 mm. In some embodiments, the thickness is constant along length 12. Optionally, the ratio of length: thickness of piece of material 12 is in the range of from about 3:1 to about 200:1, and the ratio of width:thickness is optionally in the range of from about 6:1 to about 40:1.

In some embodiments, the width of sides 26a and 26b, is in the range of from about 0.5 mm to about 15 mm.

Device 10 further comprises at least one inlet 28, such as, for example one, two, three, four, or more inlets. The inlet can have a height 25 above outer surface 20 in the range of about 0.5 about 30 mm. An inlet 28 provides fluid communication between outer surface 20 and inner surface 18, such that a fluid can be introduced into hollow area 31, for example by injection. Fluid introduced via inlet 28, is thereby directed to the target site (an area on the outer surface 33 of a bodily organ 30) along a short fluid path. Inlet 28 is optionally an aperture having dimensions sufficient for insertion of a narrow tip, such as a tip of a syringe needle. In some embodiments, the syringe needle has a gauge number of from 12 to 25, i.e. an outer diameter in the range of from about 0.5 to about 3 mm. In some embodiments, such an aperture is self-sealing, that is to say, is such that a component like an injection needle can be forced thereinto, but when the component is withdrawn, the aperture closes to substantially prevent reflux of a fluid.

Figure 1B:
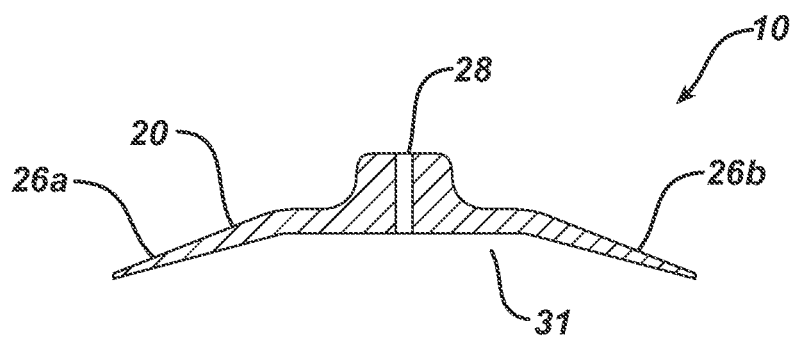
FIG. 1B is a cross-sectional view of the embodiment of the device depicted in FIG. 1A, parallel to the width dimension.

According to one exemplary embodiment of device 10 described herein, piece of flexible material 12 was prepared from Polyurethane and has length dimension 14 of about 73 mm long and width dimension 16 of about 36.4 mm wide, and three inlets 28 (the distance between the centers of the inlets is 20 mm), each inlet 28 having a height 25 above outer surface 20 of about 3.5 mm, and an aperture diameter of about 1.1 mm. The thickness of the material 12 is between 0.3 to 1.5 mm, and the inner volume of the device is about ~9770 mm$^3$. FIG. 1B is a cross-sectional view of device 10, parallel to width dimension 16. In FIG. 1B, spaced-apart sides 26a and 26b, and hollow area 31 therebetween are clearly seen.

Figure 1C:
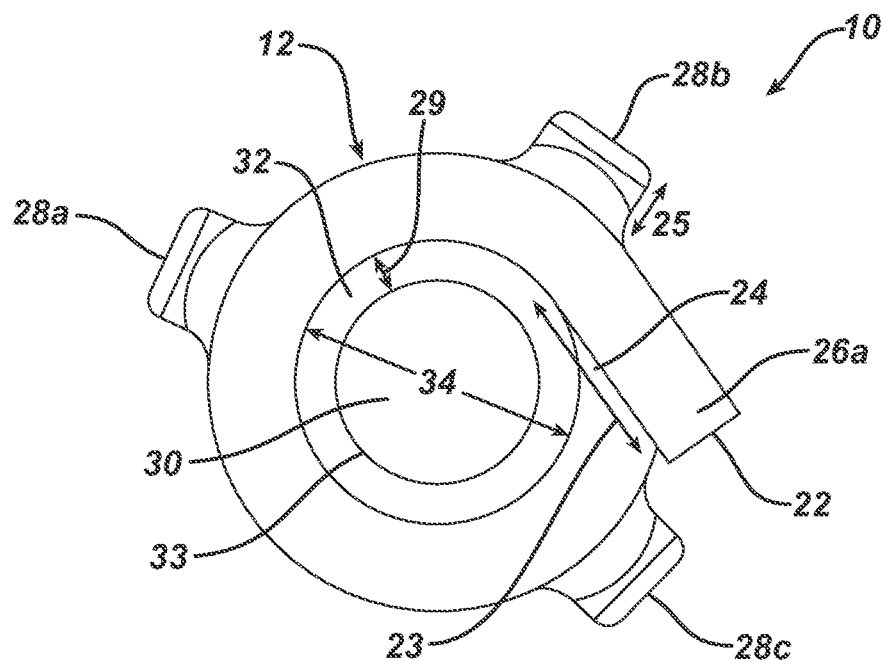
FIG. 1C is a cross-sectional side view of the embodiment of the device depicted in FIG. 1A, deployed on a bodily organ.

FIG. 1C is a cross-sectional side view of device 10 in an unconstrained state, deployed on a bodily organ 30. Piece of flexible material 12 is biased to curl to form a closed, planar spiral around at least 360 degrees around itself in an unconstrained state, such that a portion of inner surface 18 of length dimension 14 proximal to first end 22, contacts a portion of outer surface 20 of length dimension 14 proximal to second end 24 by overlapping along a portion 23 of length 14. Device 10 as shown in FIG. 1C has three inlets, 28a, 28b, 28c.

When device 10 is deployed on organ 30, as shown FIG. 1C, a gap 29, for example of height about 2 mm is constituted between an outer surface 33 of organ 30 and inner surface 18, such that an enclosed volume 32, suitable for containing a fluid, is defined between outer surface 33 of bodily organ 30 and hollow area 31 formed between inner surface 18 and sides 26a, 26b.

Figure 1D:
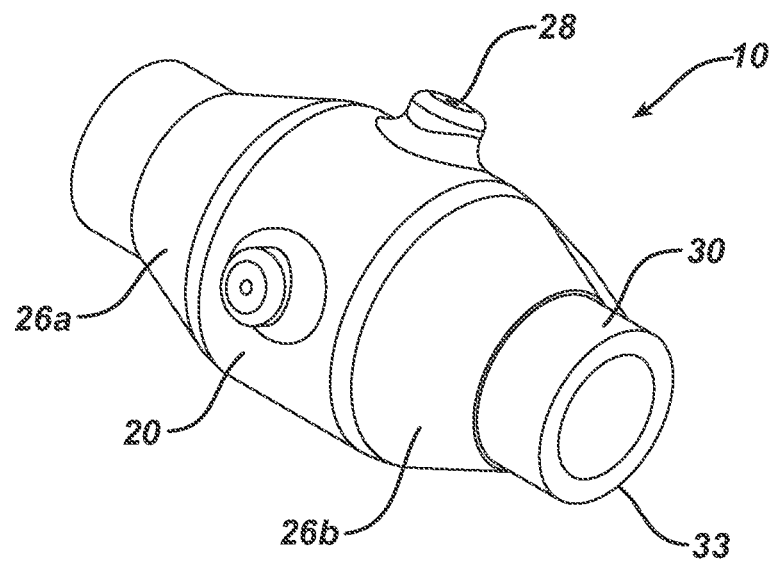
FIG. 1D is a perspective view of the embodiment of the device depicted in FIG. 1A, deployed on a bodily organ.

FIG. 1D is a perspective view of device 10 deployed on a cylindrical bodily organ 30. The inner diameter 34 of device 10 (shown in FIG. 1C) adjusts itself to the dimensions of outer surface 33 of an organ on which it is deployed, such as the outer diameter of cylindrical organ 30, such that a single device 10 may be suitable to encircle a variety of organs 30 having different outer dimensions, to implement embodiments of the teachings herein. The elasticity and bias of piece of flexible material 12 is optionally such that the bottom portions of each of sides 26a and 26b maintain uninterrupted contact around a substantially complete circumference of outer surface 33 of organ 30. As is clear to a person having ordinary skill in the art, for organs 30 having relatively smaller dimensions, inner diameter 34 is relatively small, and portion of overlap 23 is relatively long.

In contrast, for organs 30 having relatively large dimensions, inner diameter 34 is relatively large, the point where first end 22 first overlaps second end 24 is relatively close to the tip of first end 22, and portion of overlap 23 is relatively short.

The device can be delivered to the desired location by any suitable means including, but not limited to, open surgery, and minimally invasive procedures (MIS) such as laparoscopy. In one embodiment of the invention, an incision is made proximal to the target organ and the device is deployed on the target organ via the incision. The patient can receive local, regional or general anesthesia.

The term "open surgery" typically refers to surgery wherein the surgeon gains direct access to the target organ via a relatively large incision. As used herein the term "minimally invasive procedure" typically means a procedure wherein the surgeon gains access to the target organ via small incisions or through a body cavity or anatomical opening e.g. via laparoscopy. The device can be delivered to the target organ through a narrow lumen e.g. trocar in a folded form and unwound during deployment on the target organ.

For use, piece of material 12 of device 10 is first unwound, for example manually, so that ends 22 and 24 do not overlap and there is an open gap between ends 22 and 24, so that piece of material 12 is in the shape of an open curve. Piece of material 12 is maneuvered so that ends 22 and 24 pass on either side of organ 30. Piece of material 12 is released from constraint so that spaced-apart curved sides 26a and 26b contact and encircle outer surface 33 of organ 30, substantially as depicted in FIG. 1C, where first end 22 overlaps second end 24 along portion of overlap 23 to take up any excess length.

A curable fluid composition can then be introduced via inlet 28 into gap 29 defined by inner surface 18 of device 10 and outer surface 33 of organ 30 between sides 26a and 26b. In one embodiment of the invention flexible material 12 is a shape memory material that "remembers" its original, cold-forged shape.

Referring now to FIGS. 2A-2D, there is shown an embodiment 40 of a device suitable for applying a curable fluid composition to encircle a bodily organ.

Figure 2A:
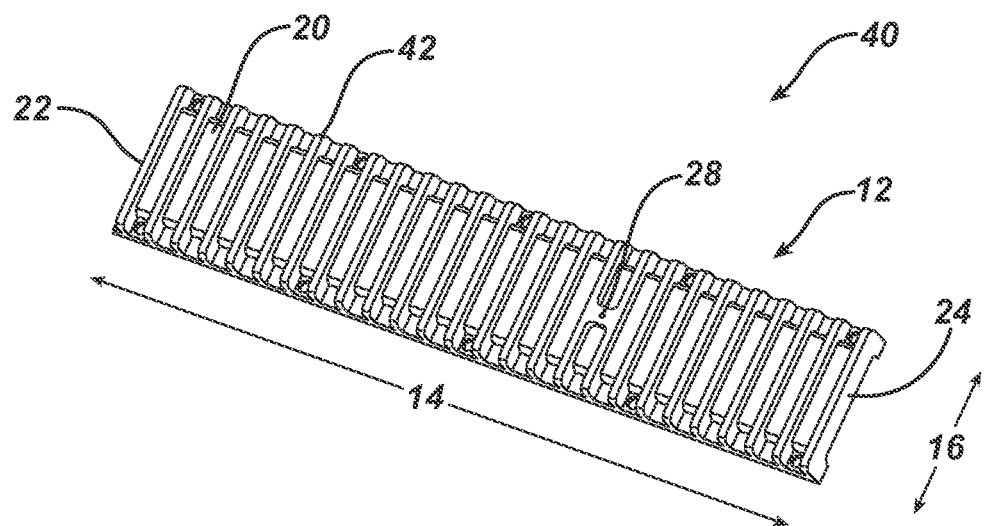
FIG. 2A is a top perspective view of an alternative embodiment of the device as described herein, in an open configuration.
Figure 2B:
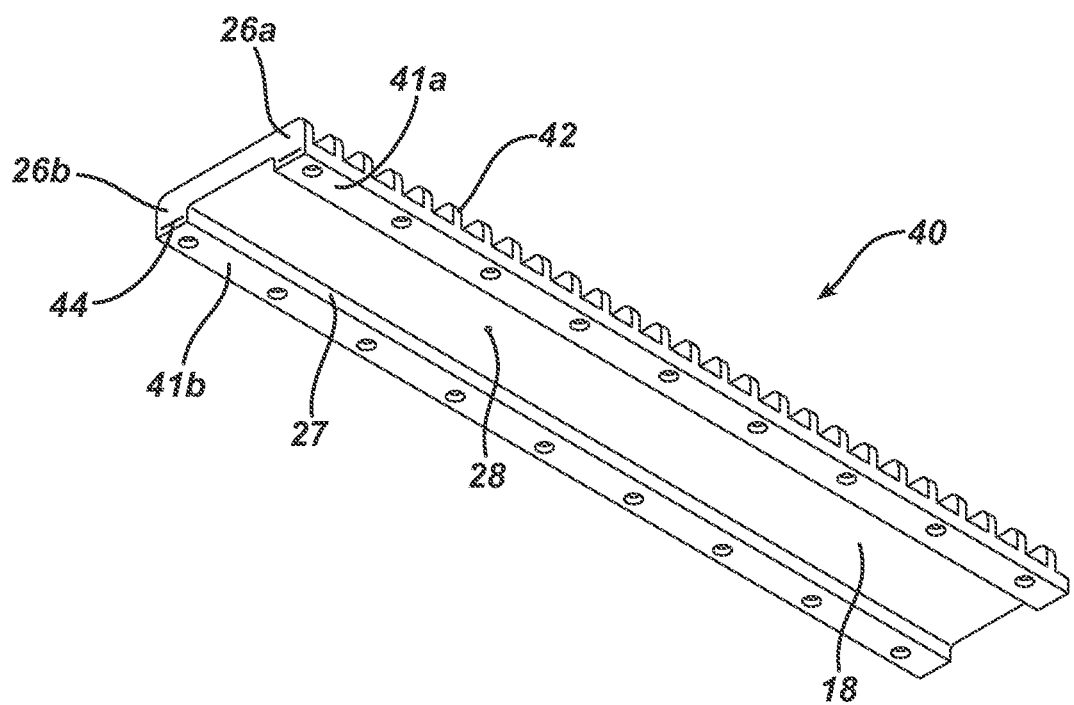
FIG. 2B is a bottom perspective view of the embodiment of the device depicted in FIG. 2A in an open configuration.
Figure 2C:
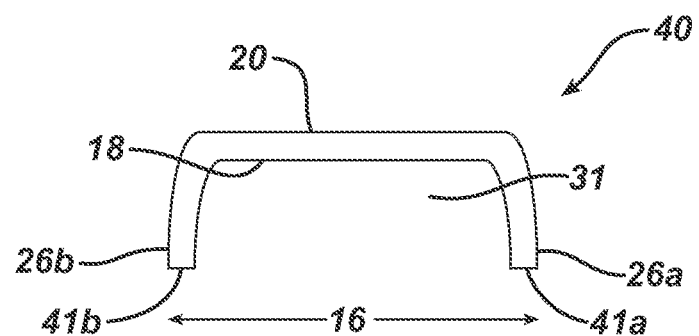
FIG. 2C is a cross-sectional side view of the embodiment of the device depicted in FIG. 2A in an open configuration.
Figure 2D:
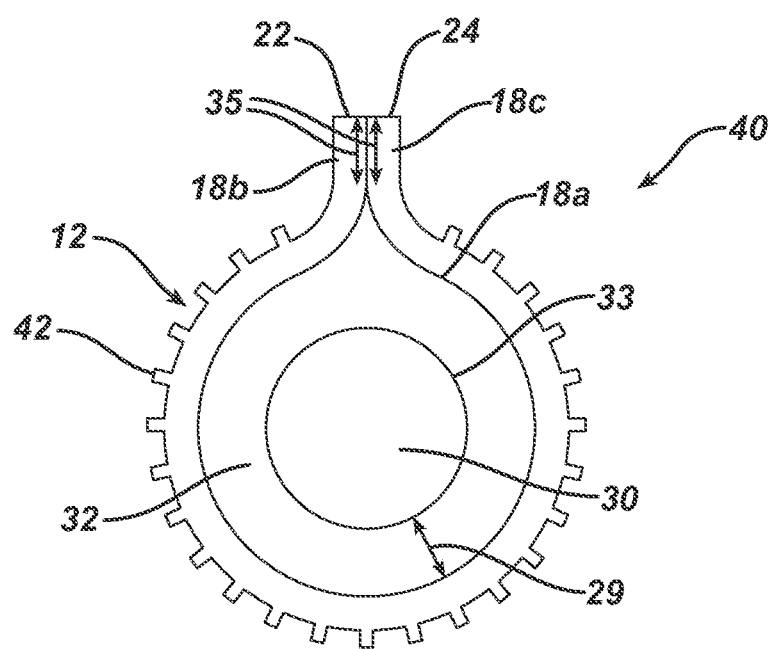
FIG. 2D is a cross-sectional side view of the embodiment of the device depicted in FIG. 2A, deployed on a bodily organ.

FIG. 2A is a top perspective view of device 40. FIG. 2B is a perspective bottom view of device 40. FIG. 2C is a cross-sectional side view of device 40. FIG. 2D is a cross-sectional side view of device 40 deployed on a bodily organ 30.

Device 40 comprises a monolithic piece of a flexible material 12, having a length dimension 14, and a width dimension 16, an inner surface 18 and an outer surface 20, forming a substantially straight, quadrilateral strip e.g. a rectangular strip in an undeployed state. Length dimension 14 has a first end 22 and a second end 24. Width dimension 16 has two spaced-apart sides 26a, 26b, such that a hollow area 31 is formed between inner surface 18 and sides 26a and 26b.

Device 40 further comprises at least one inlet 28, such as, for example one, two, three, four, or more inlets. Inlet 28 provides fluid communication between outer surface 20 and inner surface 18, such that a fluid can be introduced into the hollow area, for example, by injection. Fluid introduced via inlet 28, is thereby directed to the target site along a short fluid path.

Device 40 optionally further comprises a plurality of raised, parallel, spaced-apart bands 42 along at least a portion of outer surface 20, arranged perpendicular to length dimension 14, for providing mechanical strength, and preventing flexible material 12 from collapsing inwards when device 40 is deployed on organ 30 and/or excessively ballooning outwards when a fluid is introduced. In some embodiments, bands 42 have a height in the range of from about 3 to about 7 mm, a width in the range of from about 1 to about 3 mm, and a length in the range of from about 28 to about 34 mm. Bands 42 may be formed of the same material as piece of flexible material 12 as specified above, or of a different material.

As seen in FIG. 2B, device 40 optionally further comprises at least one plastically deformable strip 44 functionally associated with inner surface 18 and/or with a surface (e.g. a lower surface) of at least one of spaced-apart sides 26a, 26b. Strip 44 optionally is or comprises a metal, such as, for example, copper, aluminum, tin, platinum, zinc, iron and nickel, or alloys comprising such metals. In one embodiment of the invention, device 40 comprises two plastically deformable strips 44, each functionally associated with a lower surface of one of spaced-apart sides 26a, 26b. Further alternatively, each of sides 26a, 26b is optionally formed with a longitudinal slot 27 for insertion therein of strip 44. Strip 44 is optionally provided along the entire length of inner surface 18 and/or a surface of at least one or sides 26a, 26b, or along part of surface 18 and/or sides 26a, 26b.

Strip 44 allows the lower surfaces of sides 26a and 26b, that contact outer surface 33 of an organ 30 during use of device 40, to be bent into a desired shape, in order to fit the shape of a specific organ 30, including a non-cylindrical, a rigid and/or a non-rigid organ 30.

A portion 18a of the inner surface of the flexible material 12, located between ends 22 and 24 is configured to encircle an outer surface of a bodily organ 30. A portion 18b of the inner surface proximal to first end 22 is configured to intimately contact or overlap a portion 18c of the inner surface proximal to second end 24, such that inner portions 18b and 18c proximal to ends 22 and 24, respectively, are pressed one against the other when deployed on organ 30, as shown in side view in FIG. 2D. As further shown in FIG. 2D, when device 40 is deployed on organ 30, an enclosed volume 32 is defined between hollowed area 31 of device 40 and an outer surface 33 of organ 30.

For use, device 40 is wound around an outer surface 33 of organ 30, and portions 18b and 18c are brought into intimate contact along a length 35 such that an enclosed volume 32 is defined. In some embodiments, ends 22 and 24 are bent to secure one to the other. In some embodiments, ends 22 and 24 are secured one to the other using a locking mechanism (not shown).

Length dimension 14 of device 40 is optionally in the range of from about 4 to about 100 cm long, such as in the range of from about 7 to about 20 cm long. Width dimension 16 is optionally in the range of from about 1 to about 8 cm wide, or in the range of from about 4 to about 6 cm wide. In some embodiments, the width of sides 26a and 26b is in the range of from about 0.5 mm to about 15 mm. Length dimension 14 is optionally from 0.5 to 100 times the length of width dimension 16.

Depending on the embodiment, width dimension 16 may be constant along the entire length dimension 14 of piece of material 12, or piece of material 12 may taper along length dimension 14 such that width dimension 16 is narrower at first end 22 than at second end 24. Piece of material 12 optionally has a thickness in the range of from about 2 to about 15 mm. In some embodiments, the thickness is constant along length 12. Optionally, the ratio of length:thickness of piece of material 12 is in the range of from about 3:1 to about 500:1, and the ratio of width:thickness is optionally in the range of from about 6:1 to about 40:1.

Embodiments of the device described herein may be used to apply a curable fluid composition to encircle any bodily organ. For example, organ 30 may be a blood vessel (including an artery, such as an aorta, or a vein, such as a vena cava); an organ of the digestive system, including an esophagus, a stomach or part thereof (such as a cardia, a fundus, a body, or a pylorus), a small intestine or part thereof, (such as a duodenum, a jejunum or an ileum), a large intestine or part thereof (such as a colon, a cecum, a rectum, or an anus), a bowel, or a pancreas; a dura; an organ of the respiratory system such as a trachea; or an organ of the urinary system (such as a ureter, a urethra, a kidney, or a urinary bladder).

The device may be used to apply a curable substance to encircle a surface of a bodily organ of a patient. The term "a surface of a body part of a patient" refers to an external surface of the body that can be seen by unaided vision and to a surface of an internal body part which is a part of the internal anatomy of an organism. The surface can be a bleeding or a non-bleeding site.

The device can be used for applying a curable substance to encircle a bodily organ in order to decrease the risk of postoperative adhesion formation.

The term "adhesion" refers to an abnormal attachment between tissues and/or organs. Typically, adhesions occur after surgical procedures such as following rough manipulation of tissues; following tissue surface drying; and/or due to the presence of reactive foreign bodies (e.g. suture materials, talc powder or lint residues) in the operated area.

Organ 30 may be an anastomized organ (i.e. an organ that was subjected to an anastomosis surgical procedure), wherein anastomosis was achieved, for example, by stapling or suturing, and a curable fluid composition is applied onto the staple/suture line for reinforcement and/or to prevent leakage from the anastomized organ.

The term "anastomosis" typically refers to a surgical procedure which is used to reconnect two or more sections of an organ or tissue.

The term "staple or suture" includes any fastener which is used for closing a wound such as, but not limited to, staple, clip, pin, hook, suture and the like.

The terms "leak" and "leakage" refer to the escape or passage of a substance e.g. fluid, viscous material and/or air e.g. through a tear, aperture, bore, fissure, puncture, hole, crack, opening, slit, gap, perforation, fracture, puncture or rupture in a tissue.

In one embodiment of the invention, the device is used to encircle a blood vessel with the curable fluid composition for hemostasis.

The term "hemostasis" refers to the ability of an agent to stop the bleeding from an injured blood vessel and/or to contribute to keeping the blood contained within the blood vessel.

In one embodiment of the invention, organ 30 is a hollow organ, i.e. an organ comprising a cavity. A hollow organ can be filled with air, fluid, and/or solids. In some such embodiments, organ 30 is brought to a rigid state, for example, by inflating with a fluid. The fluid may comprise a liquid and/or a gas. In some such embodiments, following anastomosis by stapling, a rigid state is achieved by keeping the stapler inside the cavity of the hollow organ while the device as described herein is deployed to encircle the organ, and the curable fluid is introduced into the gap 29. In one embodiment of the invention, device 10 is for use on a rigid organ, while device 40 is for use on a rigid or non-rigid organ.

For use on an esophagus or pylorus of a stomach of a human adult, length dimension 14 of flexible material 12 is optionally about 7 cm long. For use on a small intestine of a human adult, length dimension 14 of flexible material 12 is optionally about 13 cm long. For use on a large intestine or a colon of a human adult, length dimension 14 of flexible material 12 is about 20 cm long.

Since flexible material 12 of device 10 is biased to curl to form a closed, planar spiral, which is able to self-adjust to encircle organs of varying diameter, a single device 10 may optionally be used with organs of different dimensions, such that in the case of a smaller organ, a greater degree of overlap of first end 22 over second end 24 will occur.

In the case of device 40, the length of inner portions of 18b and 18c which are brought into intimate contact when device 40 is deployed on organ 30, may be increased or decreased in accordance with the dimensions of the outer surface of organ 30, such that a single device 40 may be used with organs of different dimensions, such that in the case of a smaller organ, a greater length 35 of inner portions 18b and 18c are brought into intimate contact.

In some embodiments, curable fluid compositions useful for application using embodiments of the device described herein comprise a single component, which may be cured, for example, by application of heat, ultraviolet radiation or electron beams.

As used herein, the term "fluid" refers to any biological fluid (e.g. fluid which derives from living organisms or which is manufactured by recombinant technology) and/or chemical fluid (e.g. fluid which is chemically synthesized).

In some embodiments, curing of the curable fluid composition occurs within a time range of from a few milisec-onds to a few minutes, for example in the range of from 2 miliseconds to 10 minutes.

In some embodiments, the curable fluid composition comprises at least two components. In some embodiments comprising at least two components, a first of the two components is activated by a second of the two components. For example, the first component optionally comprises fibrinogen, and the second component optionally comprises an agent which activates fibrinogen, such as, for example, thrombin or a substance obtainable from snake venom, such that a fibrin polymer is formed upon curing of the curable fluid composition. Additional, non-limiting examples of two components of the curable fluid composition described herein include alginate and calcium; chondroitin sulphate and an acid such as hyaluronic acid.

For embodiments wherein the curable fluid composition comprises fibrinogen and thrombin components, one or both of the components can optionally be prepared from an initial blood composition. The blood composition can be whole blood or blood fractions, i.e. a fraction of whole blood such as plasma. The origin of the fibrinogen and thrombin can be autologous whereby they would be manufactured from the patient's own blood or from pooled blood or blood fractions. It is also possible that the protein components are prepared by recombinant methods.

In one embodiment of the invention, the fibrinogen component comprises a biologically active component (BAC) which is a solution of proteins derived from blood plasma, optionally further comprising anti fibrinolytic agents such as tranexamic acid and/or stabilizers such as arginine, lysine, pharmaceutically acceptable salts thereof, or mixtures thereof. BAC is optionally derived from cryoprecipitate, in particular concentrated cryoprecipitate. The term "cryoprecipitate" refers to a blood component which is obtained from frozen plasma prepared from whole blood, recovered plasma or from source plasma which is collected by plasmapheresis. A cryoprecipitate is optionally obtained when frozen plasma is slowly thawed in the cold, typically at a temperature of 0-4° C., resulting in the formation of precipitate that contains fibrinogen and factor XIII. The precipitate can be collected, for example, by centrifugation and dissolved in a suitable buffer such as a buffer containing 120 mM sodium chloride, 10 mM trisodium citrate, 120 mM glycine, 95 mM arginine hydrochloride, 1 mM calcium chloride. The solution of BAC optionally comprises additional factors such as for example factor VIII, fibronectin, von Willebrand factor (vWF), vitronectin, etc. for example as described in U.S. Pat. No. 6,121,232 and WO9833533. The composition of BAC optionally comprises stabilizers such as tranexamic acid and arginine hydrochloride. The amount of tranexamic acid in the solution of BAC is optionally in the range of from about 80 to about 110 mg/ml. The amount of arginine hydrochloride is optionally in the range of from about 15 to about 25 mg/ml.

Optionally, the solution is buffered to a physiological compatible pH value. The buffer comprises glycine, sodium citrate, sodium chloride, calcium chloride and water for injection as a vehicle. Glycine is optionally present in the composition at a concentration in the range of from about 6 to about 10 mg/ml; sodium citrate is optionally present at a concentration in the range of from about 1 to about 5 mg/ml; sodium chloride is optionally present at a concentration in the range of from about 5 to about 9 mg/ml; and calcium chloride is optionally present at a concentration in the range of from about 0.1 to about 0.2 mg/ml.

In one embodiment of the invention, the fibrinogen component is derived from blood. In another embodiment of the invention, the concentration of plasminogen and/or plasmin in the blood derived component comprising fibrinogen is lowered. The removal of plasmin and plasminogen from the blood derived component can be carried out as described in U.S. Pat. No. 7,125,569 and WO02095019.

The thrombin component optionally comprises human thrombin (800-1200 IU/ml), calcium chloride, human albumin, mannitol, sodium acetate and water for injection.

Components of a fibrin sealant comprising fibrinogen and thrombin are available from manufacturers such as OMRIX e.g. EVICEL®, QUIXIL®, Baxter e.g. TISEEL®; CSL e.g. Beriplast® and the like. In one embodiment, the fibrinogen and thrombin components are manufactured from pooled human source plasma and provided as a single use kit consisting of two vials: one vial contains the fibrinogen component (BAC1 or BAC2) and another vial contains the thrombin component. The components of the fibrin sealant may be mixed in any desired range of ratios in the method of the invention. For example, when the concentration of fibrinogen in the fibrinogen component is 40-85 mg/ml and the thrombin concentration in the thrombin component is about 800-1200 IU/ml, the two components can be mixed in a ratio of 11:1, 7:1, 6.5:1, 5:1, 3:1, 1:1, respectively, and so on.

In some embodiments, the concentration of the fibrinogen used in the method of the invention is about 30.5 mg/ml, and the concentration of the thrombin used in the method of the invention is about 584 IU/ml. The mentioned concentrations are following mixing of the two components.

In some embodiments, the concentration of the fibrinogen used in the method of the invention is about 51.5 mg/ml, and the concentration of the thrombin used in the method of the invention is about 180 IU/ml. The mentioned concentrations are following mixing of the two components. The components of the fibrin sealant can comprise one or more additives such as, but not limited to, biologically active molecules such as antibiotics, anti inflammatory agents, chemotherapy agents, growth factors, anti-cancer drugs analgesics, proteins, hormones, antioxidants and the like.

For curable fluid compositions comprising at least two components, each of the components may optionally be introduced into volume 32 via the same inlet 28, either simultaneously or sequentially. For example, the components may be introduced via inlet 28 by injection, with the two components injected simultaneously e.g. using a double lumen tip, or sequentially e.g. by use of two single lumen tips. Also, the two components may be mixed before injected. Alternatively, the components may optionally be introduced simultaneously, sequentially or mixed via at least two different inlets 28a, 28b. According to some embodiments, the components may be introduced via a tube e.g. having a bi-lumen arrangement which is connected to the inlet.

In some embodiments, a first portion of one or both components of the curable fluid composition is optionally introduced into volume 32 via a first inlet 28a and a subsequent portion of one or both components is introduced via at least a second inlet 28b. Second inlet 28b is optionally located diametrically opposite to first inlet 28a, or separated from first inlet 28a by, for example, 90-180 degrees when the device is deployed, such that delivery of the fluid composition around the entire circumference of the organ is achieved more efficiently. In the event of blockage of first inlet 28a following introduction of a first portion of the fluid composition, the remainder of the fluid composition may be introduced via second inlet 28b.

Hence, for example, a double lumen tip may be inserted into a first inlet 28a to introduce a first portion of each of the two components into volume 32, then the tip can be removed and inserted into a second inlet 28b for introduction of the remaining portion of each of the two components.

Alternatively, two or more tips/injectors may optionally be inserted simultaneously or sequentially into at least two different inlets 28a, 28b, for introduction of at least two portions of the fluid into volume 32. Each injector optionally comprises a double lumen tip for simultaneous introduction of each of the at least two components, or a single lumen tip for introduction of one of the at least two components, such that at least one additional single lumen tip is required for sequential introduction of a second component.

In one embodiment of the invention, following introduction of the curable fluid composition into volume 32, the fluid is allowed to cure.

Following completion of the curing process, device 10, 40 may be removed. Alternatively, in the case of a device wherein flexible material 12 comprises a biodegradable substance, device 10, 40 may be allowed to remain deployed around organ 30.

EXAMPLES

Materials and Methods:
Fibrinogen and Thrombin Components.

The fibrinogen component used in the experiments described below is the Biological Active Component 2 (BAC2) of Evicel® fibrin sealant (Omrix Biopharmaceuticals Ltd.), and the thrombin component used is the thrombin component of Evicel® fibrin sealant (Omrix Biopharmaceuticals Ltd.). The two components were used in a 1:1 volume ratio—the final fibrinogen concentration applied was 30.5 mg/ml, and the final thrombin concentration applied was 584 IU/ml.

Concentrated fibrin sealant. BAC2 and thrombin components of Evicel® fibrin sealant were used in a 6.5:1 volume ratio—the final fibrinogen concentration applied was 51.5 mg/ml, and the final thrombin concentration applied was 180 IU/ml.

Burst pressure test.

The burst pressure provides an indication of the ability of a tested formulation to adhere to an organ tissue and maintain its mechanical integrity up to the pressure point in which a burst of the seal occurs, resulting in immediate loss of pressure and visible water leakage. The burst pressure test was carried out essentially as described in Vilela et al. ["What Is Important For Continent Catheterizable Stomas: Angulations or Extension?" Int Braz J Urol. 2007; Vol. 33(2): 254-263] to determine and evaluate the ability of the sealant to effectively seal the organ and withstand pressure. Briefly, a specially designed aluminum pipe of length 27 cm, provided with holes, was inserted into a tubular segment of pig ileum of length 25-30 cm. The tubular segment was sealed at both ends by attachment to the pipe using plastic discs, which were tightened using metal screws, such that a void area was formed between the segment of ileum and the aluminum pipe. A 5-10 mm incision was formed perpendicular to the intestine length using a sharp blade, and then the fibrin sealant formulation to be tested (the formulations are elaborated below) was applied onto the incision area. Application of the fibrin sealant onto the incision was carried out by dripping (from a distance of 10 cm from the target using the Evicel® applicator device without gas; the dripping rate was ~4 ml/minute through a template frame (20×30 mm; 6 cm$^2$) which was placed around the incision area), spraying [(at 25 psi from a distance of 10 cm from the target using the Evicel® applicator device; the spraying rate was ~4 ml/minute) through a template frame (20×30 mm; 6 cm$^2$) which was placed around the incision area], or by using the device described herein. Application by dripping or spraying was carried out only onto the incision site, while fibrin sealant delivered using the device described herein was carried out around a circumference (i.e. 360 degrees) of the ileum in the incision area.

The fibrin was left to cure at room temperature (about 20-25° C.) for 10 minutes.

In the next step, the aluminum pipe was connected to a water source, and water was allowed to flow into the aluminum pipe, such that water entered into the void area through the holes provided in the pipe, in a way that backflow of water into the aluminum pipe was prevented.

Once water entered into the void area, the water pressure increased until the seal of the incision burst, and a sharp drop in pressure was observed. The observed pressure level was continuously monitored using a pressure gauge (D-logmate 590 MRC Israel) which was connected to the liquid flow line. The maximum pressure prior to the pressure drop was recorded and considered as the burst pressure. Typically, a higher burst pressure value indicates a greater sealing strength.

Example 1: The Structure of the Device According to the Invention

A device as shown in FIG. 1A-1D was used in Examples 2-4 below. The device was prepared from Polyurethane. The thickness of the device was between 0.3 to 1.5 mm. The device had a length of 73 mm and a width of 36.4 mm. The device had 3 inlets. The distance between the centers of the inlets was 20 mm. The height of the inlets above the outer surface of the device was 3.5 mm and the diameter of the aperture was 1.1 mm. The inner volume was about ~9770 mm$^3$.

Example 2: Application of Fibrin Sealant onto an Incision Area by Using the Device of FIG. 1

In the following experiment, the efficacy of a device according to the invention in applying fibrin sealant onto a circumference of a target area was explored. The performance of Evicel® following application by the device of FIG. 1, was evaluated using the burst test described above.

A device as described in Example 1 was used. Spraying and dripping applications were used as reference.

In this experiment, a 5 mm incision was made and the following application methods were monitored:

I: Evicel® applied by spraying equal volumes of fibrinogen and thrombin components, with a total volume of 2.4 ml;

II: Evicel® applied by dripping equal volumes of fibrinogen and thrombin with a total volume of 2.4 ml;

III: Evicel® applied by introducing equal volumes of fibrinogen and thrombin components with a total volume of 6 ml using the device described in Example 1.

Four replicates for each treatment were carried out.

The results of the burst pressure test for each application method are presented in Table 1 below.

TABLE 1

Burst pressure obtained following application of fibrin sealant in different application methods.

| | Burst pressure (mmHg) | | |
| --- | --- | --- | --- |
| | Application by spraying | Application by dripping | Application by using the device according to the invention |
| 1 | 35 | 52 | 58 |
| 2 | 41 | 17 | 32 |
| 3 | 35 | 11 | 70 |
| 4 | 30 | 25 | 107 |
| Average | 35.3 | 26.3 | 66.8 |
| Standard deviation | 4.5 | 18.1 | 31.2 |

It was observed that a higher pressure was needed in order to burst the fibrin seal on the intestine tissue when fibrin was formed using Evicel® with the device according to the invention, allowing to encircle the intestine, as compared to the pressure needed to burst the fibrin seal when Evicel® was applied by either spraying or dripping onto the incision on a 20 mm×30 mm area, indicating that sing the device according to the invention to form a fibrin seal results in a greater adhesive force.

It was therefore found that the sealing strength when using the device according to the invention was superior as compared to the sealing strength obtained following application by dripping or spraying.

Example 3: Application of Different Fibrin Sealant Formulations onto a Sutured Incision Line by Using the Device of FIG. 1

In the previous example it was shown that using a device according to the invention for application of fibrin sealant results in superior sealing compared to application by spraying or dripping.

In the following experiment, application of two different fibrin sealant formulations was tested using the device described in Example 1. The performance of the formulations was evaluated using the burst test described above; spraying application was used as reference.

In this experiment, an incision line of 10 mm was made and prior to application of the fibrin sealant, the incision line was sutured along its midline with one stitch of 3-0 suture (3-0 SS-684 c-14, Ethicon).

The following formulations and application methods were monitored:

I: Evicel® applied by spraying equal volumes of fibrinogen and thrombin components in a total volume of 2 ml.

II: Evicel® applied by introducing equal volumes of fibrinogen and thrombin in a total volume of 4 ml using the device of Example 1.

III: Concentrated fibrin sealant applied by introducing fibrinogen and thrombin components in a total volume of 4 ml using the device of Example 1.

Four replicates for each treatment were carried out.

The results are presented in Table 2 below.

TABLE 2

Burst pressure obtained following application of different fibrin sealant formulations in different methods.

| | Burst pressure (mmHg) | | |
| --- | --- | --- | --- |
| | Application of Evicel® by spraying | Application of Evicel® using the device according to the invention | Application of concentrated fibrin sealant using the device according to the invention |
| 1 | 63 | 12 | 109 |
| 2 | 6 | 100 | 97 |
| 3 | 31 | 20 | 140 |
| 4 | 59 | 41 | 86 |
| Average | 39.8 | 43.3 | 108.0 |
| Standard deviation | 26.6 | 39.8 | 23.3 |

The results obtained in this experiment corroborate the previous results and show that applying Evicel® on a suture line using the device according to the invention results in superior sealing as compared to the sealing obtained by the spraying method.

Also, it was observed that a higher pressure was needed in order to burst the fibrin seal on the intestine tissue when fibrin was formed using the high concentration fibrin sealant and applied with a device according to the invention as compared to the pressure needed when Evicel® fibrin sealant compositions was applied by either spraying or using the device according to the invention.

Thus, application of high concentration fibrin sealant using the device according to the invention gave significantly superior results compared to the other treatments (P-value>0.05, T test).

Example 4: Application of Concentrated Fibrin Sealant Formulation to an Incision Area Using Spray or the Device According to the Invention In the previous Example it was shown that forming a fibrin seal using the concentrated fibrin sealant and using a device according to the invention resulted in superior sealing strength. In the following experiment, the performance of concentrated fibrin sealant following use of the device of Example 1 was compared to that of the concentrated fibrin sealant when applied by spraying. The performance was evaluated by using the burst test described above.

In this experiment, a 5 mm incision was carried out, and the concentrated fibrin sealant was applied by spraying (a total volume of 2 ml) or by using the device according to the invention (a total volume of 4 ml) onto the incision as described above.

Four replicates for each treatment were carried out. The results are presented in Table 3 below.

TABLE 3

Burst pressure obtained following application of different fibrin sealant formulations onto an incision area in different methods.

| | Burst pressure (mmHg) | |
| --- | --- | --- |
| | Application of concentrated fibrin sealant by spraying | Application of concentrated fibrin sealant using the device according to the invention |
| 1 | 99 | 115 |
| 2 | 115 | 134 |
| 3 | 90 | 118 |
| 4 | 83 | 132 |
| Average | 96.8 | 124.8 |
| Standard deviation | 13.8 | 9.6 |

It was observed that a higher pressure was needed in order to burst the fibrin seal on the intestine tissue when concentrated fibrin sealant was applied using the device according to the invention which allows to encircle with sealant the entire intestinal tissue, compared to the pressure needed when the spray treatment was used onto the incision on a 20 mm×30 mm area (P-value>0.05, T test). Thus, the treatment with the device according to the invention and concentrated fibrin sealant (as defined above) is superior as compared to the treatments with spray.

It was therefore found that the adhesive force is improved when using a device according to the invention and the concentrated fibrin sealant.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the scope of the appended claims.

Citation or identification of any reference in this application shall not be construed as an admission that such reference is available as prior art to the invention.

The invention claimed is:

1. A device suitable for application of a curable fluid composition to encircle a bodily organ, wherein prior to deployment on a bodily organ the device comprises:
    a monolithic piece of a flexible material having a length dimension with an inner surface and an outer surface, a first end and a second end, a width dimension, and two spaced-apart sides, wherein when said piece of flexible material is unconstrained it forms a planar spiral, such that a portion of said length dimension proximal to said first end overlaps a portion of said length dimension proximal to said second end,
    said inner surface defining a hollow area between said two spaced-apart sides; and at least one inlet providing fluid communication between said outer surface and said inner surface, for introduction of said fluid into said hollow area, the device deployable around said bodily organ such that when said portion of said length dimension proximal to said first end contacts said portion of said length dimension proximal to said second end, an outer surface of said bodily organ and said hollowed area define an enclosed volume encircling said bodily organ, said enclosed volume suitable for containing said fluid therein.

2. The device of claim 1, configured so that when deployed around said bodily organ, a portion of said length dimension between said first end and said second end encircles said bodily organ, and an inner surface of said piece of flexible material proximal to said first end intimately contacts an inner surface of said piece of flexible material proximal to said second end, thereby defining said enclosed volume.

3. The device of claim 1, wherein said curable fluid composition comprises at least two components, and wherein a first of said at least two components is activated by a second of said at least two components.

4. The device of claim 3, wherein said first component comprises fibrinogen and said second component for activation of said fibrinogen comprises thrombin.

5. The device of claim 4, wherein a concentration of said fibrinogen is 51.5 mg/ml and a concentration of said thrombin is 180 IU/ml.

6. The device of claim 1, wherein said flexible material is selected from the group consisting of a non-biodegradable material, a biodegradable material, and combinations thereof.

7. The device of claim 1, wherein said bodily organ is a hollow organ.

8. The device of claim 1, wherein said bodily organ is selected from the group consisting of a blood vessel, an organ of the digestive system, an organ of the urinary system, and a dura.

9. A method for applying a curable fluid composition to encircle a bodily organ, the method comprising:
providing a device according to claim 1,
deploying said device around said bodily organ so that said portion of said length dimension proximal to said first end contacts said portion of said length dimension proximal to said second end, thereby defining, between an outer surface of said bodily organ and said hollowed area, an enclosed volume encircling said bodily organ; and
introducing said curable fluid composition into said enclosed volume through said at least one inlet.

10. The method of claim 9, wherein said curable fluid composition comprises at least two components, wherein said two components are introduced substantially simultaneously through the same of said at least one inlet.

11. The method of claim 9, wherein introducing said curable fluid composition comprises injecting said curable fluid composition through said at least one inlet.

12. The method of claim 9, further comprising allowing said curable fluid composition to cure, and removing said device subsequent to curing of said curable fluid composition.

13. The method of claim 9, wherein said bodily organ is a hollow organ.

14. The method of claim 13, wherein said hollow organ is in a rigid state.

15. The method of claim 9, wherein said bodily organ is an anastomized bodily organ, and wherein said bodily organ is anastomized by a method selected from the group consisting of stapling and suturing.

16. The method of claim 15, wherein said bodily organ is anastomized by stapling and said stapler is present in said organ during said applying of said curable fluid composition to provide a rigid state of said bodily organ.

* * * * *